(12) United States Patent
Morf

(10) Patent No.: US 6,999,555 B2
(45) Date of Patent: Feb. 14, 2006

(54) SYSTEMS AND METHODS FOR PROCESSING DATA

(75) Inventor: Daniel Morf, Buch am Irchel (CH)

(73) Assignee: Varian Medical Systems Imaging Laboratory GmbH, (CH)

( * ) Notice: Subject to any disclaimer, the term of this patent is extended or adjusted under 35 U.S.C. 154(b) by 92 days.

(21) Appl. No.: 10/663,009

(22) Filed: Sep. 15, 2003

(65) Prior Publication Data

US 2005/0058237 A1     Mar. 17, 2005

(51) Int. Cl.
*G01N 23/02*     (2006.01)
*G01N 23/083*     (2006.01)

(52) U.S. Cl. ....................... 378/62; 378/901
(58) Field of Classification Search ............ 378/4, 378/8, 15, 19, 62, 65, 901
See application file for complete search history.

(56) References Cited

U.S. PATENT DOCUMENTS

| 5,077,769 | A  | * | 12/1991 | Franciose .................. 378/98.2 |
| 6,490,335 | B1 | * | 12/2002 | Wang et al. .................. 378/15 |
| 6,522,714 | B1 | * | 2/2003  | Wang et al. .................. 378/15 |
| 6,856,666 | B2 | * | 2/2005  | Lonn et al. .................... 378/8 |

* cited by examiner

*Primary Examiner*—David V Bruce
(74) *Attorney, Agent, or Firm*—Bingham McCutchen LLP

(57) ABSTRACT

A method for processing data in a radiation procedure includes obtaining operation data, and formatting the operation data into a set of image data, wherein the operation data comprises one or a combination of a gantry angle, a patient position, a patient orientation, radiation dose rate, radiation dose fraction, beam pulse rate, beam energy, time when beam was activated, time when beam was deactivated, and beam variation (if any) during an image readout. Also machine axis information, machine status info and operation data from other systems like for instance the RPM system may be included. A method of processing data in a radiation procedure includes obtaining operation data, obtaining an image data, and combining the operation data with the image data in substantially real time.

53 Claims, 4 Drawing Sheets

SYSTEMS AND METHODS FOR PROCESSING DATA

BACKGROUND OF THE INVENTION

1. Field of the Invention

The field of the invention relates to methods and systems for data processing, and more particularly, to systems and methods for processing data obtained during a radiation procedure.

2. Background of the Invention

Radiation therapy involves medical procedures that selectively expose certain areas of a human body, such as cancerous tumors, to doses of radiation. The purpose of the radiation therapy is to irradiate the targeted biological tissue such that undesirable tissue is destroyed. Radiation has also been used to obtain image of tissue for planning or treatment purposes.

During a radiation planning session, radiation treatment planning is performed before treatment radiation is delivered to a patient. This allows an accurate and precise dosage of radiation to be delivered to a patient. During the planning session, configuration data, such as location, size, and shape of a target object, may be acquired using a x-ray system. Images of the patient may also be acquired using an imaging device, such as a camera, so that a physiological movement of the target object can be monitored. The planning process then generates a radiation treatment plan based on a synchronization of the configuration data with the image data. Changes to the treatment plan for further optimization can also be developed during the planning session.

When the radiation treatment plan is determined, the radiation treatment plan can be verified before a full dose radiation delivery may be performed. During a radiation treatment planning verification session, the patient is irradiated with a low energy x-ray image beam to determine an image of a target region, and a high energy, low intensity radiation beam for generating radiation absorption data. While the patient is being irradiated with the image beam, operation data, such as radiation intensity or absorption data, gantry angle, and patient position are recorded and time stamped. The recorded operation data are then correlated with the image data at a later time to verify the radiation treatment plan.

During a radiation treatment session, a desired radiation dosage is delivered to the patient according to the verified radiation treatment plan, and operation data and image data may be obtained during the treatment session. The operation data may be associated with the image data at a later time to verify that a prescribed distribution and magnitude of radiation dose has been correctly delivered to the target region.

In current methods, the combining and/or associating of image data with operation data is not performed in real time. Operation data are generally captured using a first system, time stamped, and stored in a first memory, and image data are captured using a second system, time stamped, and stored in a second memory. The stored operation data and the stored image data are then interpolated and correlated with each other at a later time using a third system. As such, current methods require multiple systems to perform synchronization of image data and operation data, which may be difficult and costly to implement. In addition, since current methods require handling and processing of collected image data and operation data by a technician before they are synchronized, the collected data may be lost or misfiled due to human errors. Furthermore, correlating the image data with the operation data may be labor intensive, and may not be always accurate.

Accordingly, improved systems and methods for combining operation data with image data would be useful.

SUMMARY OF THE INVENTION

In accordance with one embodiment of the invention, a method of processing data in a radiation procedure includes obtaining a first set of image data, obtaining operation data, putting the operation data into a format that is the same as a format of the first set of image data, and adding the operation data to the first set of image data. In one embodiment, the first set of image data can be obtained during a radiation treatment procedure in which a treatment beam is directed towards a target region. Alternatively, the first set of image data can be obtained during a non-treatment procedure in which an imaging beam is directed towards the target region. By means of non-limiting examples, the operation data can comprise one or a combination of a gantry angle, a patient position, a patient orientation, a radiation dose rate, a radiation dose fraction, a beam pulse rate, a beam energy level, a time when a beam was activated, a time when a beam was deactivated, machine axis information, and machine status information. In one embodiment, the operation data and the first set of image data are obtained and combined automatically in substantially real time. This is beneficial in that it reduces the number of systems required to generate the combined data, and that it prevents or reduces the risk of lost of data, misfiled data, and incorrect correlation of data, since the operation data and the first set of image data are processed automatically. Combining operation data and image data in substantially real time is also advantageous in that the combined data can be made available for immediate feedback.

In accordance with another embodiment of the invention, a method for processing data in a radiation procedure includes obtaining operation data, and formatting the operation data into a set of image data. By means of non-limiting examples, the operation data can comprise one or a combination of a gantry angle, a patient position, a patient orientation, a radiation dose rate, a radiation dose fraction, a beam pulse rate, a beam energy level, a time when a beam was activated, a time when a beam was deactivated, machine axis data, and machine status information. The set of image data may be stored with other image data that are readout from an image detector, such as that associated with a radiation system or a separate imaging device.

In accordance with another embodiment of the invention, a method for processing data in a radiation procedure includes obtaining operation data, obtaining an image data, and combining the operation data and the image data in substantially real time. By means of non-limiting examples, the operation data can comprise one or a combination of a gantry angle, a patient position, a patient orientation, a radiation dose rate, a radiation dose fraction, a beam pulse rate, a beam energy level, a time when a beam was activated, a time when a beam was deactivated, machine axis data, and machine status information.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION OF THE PREFERRED EMBODIMENTS

Figure 1:
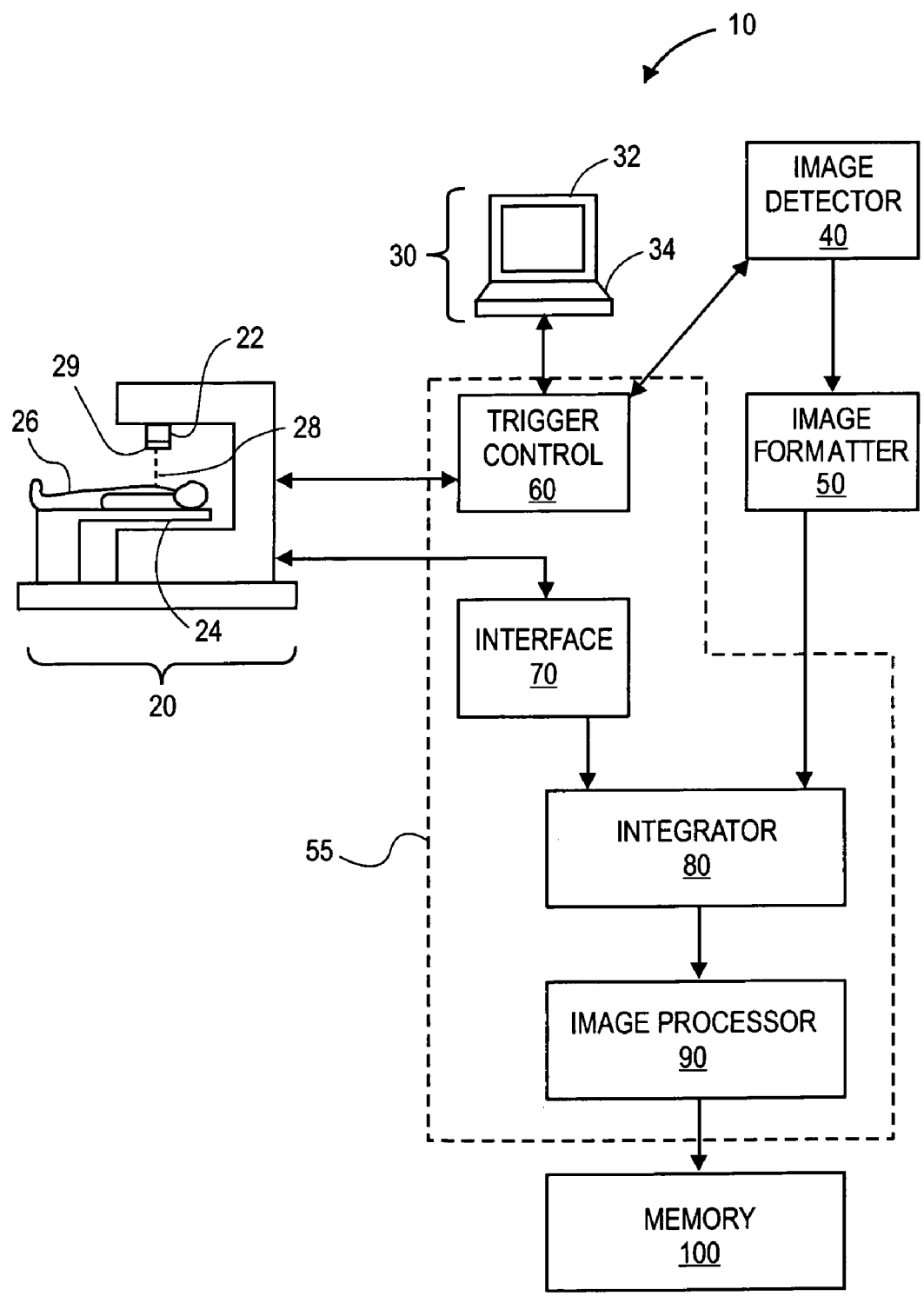
FIG. 1 illustrates a system for collecting and combining operation data and image data.

Various embodiments of the present invention are described hereinafter with reference to the figures. It should be noted that the figures are not drawn to scale and that elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated.

FIG. 1 illustrates a system 10 for collecting and combining operation data and image data. The system 10 includes a radiation system 20 having a radiation beam source 22 and a platform 24 for supporting a patient 26, an image detector 40, an image formatter 50 for formatting image data generated by the image detector 40, and a data integration module 55 coupled to the radiation system 20 and the image detector 40. The image formatter 50 is configured to align and/or format image signal collected from the image detector 40 such that the image signal can be used for later processing. Although the image formatter 50 is shown as a separate component, in an alternative embodiment, the image formatter 50 can be a part of the image detector 40 or a part of the data integration module 55.

During a radiation session, the radiation beam source 22 generates an x-ray beam 28 toward the platform 24, and a beam adjuster 29 in front of the beam source 22 functions to adjust the shape, size, intensity, and direction of the beam 28 reaching the patient 26 on the platform 24. In one embodiment, the beam adjuster 29 includes one or more multiple leaf collimators. In an alternative embodiment, the beam adjuster 29 includes one or more multiple leaf collimators and/or one or more single jaw collimators. The radiation system 20 also includes a control module (not shown) coupled to the beam source 22, the platform 24, and the beam adjuster 29 to control their operations. In the illustrated embodiment, the radiation system 20 is a RPM machine available at Varian Medical Systems, Inc., Palo Alto, Calif. However, the radiation system 20 can also be a computed tomography (CT) machine, a fluoroscopic system, a simulator, a Clinac machine, or other suitable systems that includes a radiation source.

In one embodiment, the beam source 22 can be of a type that generates radiation beam at a prescribed energy level. Alternatively, the beam source 22 is capable of generating radiation beams at different energy levels. For example, in one embodiment, the beam source 22 is configured to generate X-ray radiation beams at a kilo-electron-volt (keV) energy level and a mega-electron-volt (MeV) energy level. A keV energy level X-ray radiation beam is generally used for forming images of the tissues in the patient 26, and is therefore also referred to as an image beam or a diagnostic beam. An MeV energy level X-ray radiation beam is generally used for treating tissues or other in the patient 26. The MeV energy level X-ray radiation beam can also be used for forming images of the patient 26. The beam source 22 may include a single beam generation module or multiple beam generation modules. In accordance with one embodiment of the present invention, the beam source 22 includes two X-ray beam generators, one for generating the keV energy level X-ray image beams and another for generating the MeV energy level X-ray radiation beams. The two beam generators may be located in close proximity with each other or separated from each other. For example, in one embodiment, the two beam generators are so located that they project radiation beams toward the patient 26 on the platform 24 at an angle of approximately 90° from each other. In accordance with another embodiment, the beam source 22 includes a signal X-ray beam generator that is capable of generating X-ray beams at multiple energy levels. By way of example, U.S. patent application Ser. No. 10/033,327 entitled "RADIOTHERAPY APPARATUS EQUIPPED WITH AN ARTICULABLE GANTRY FOR POSITIONING AN IMAGING UNIT" and filed on Nov. 2, 2001 discloses a system with X-ray radiation sources at different energy levels. U.S. patent application Ser. No. 10/033,327 is herein expressly incorporated by reference in its entirety.

Although the image detector 40 is depicted as a separate component, the image detector 40 can be a part of the radiation application system 20. In the illustrated embodiment, the image detector 40 includes a projection detector (or detector array), such as a x-ray detector or a amorphous silicon (aSi) detector, that is secured to the radiation application system 20. The detector array has a plurality of sensor elements configured for sensing a x-ray that passes through the patient 26. Each sensor element generates an electrical signal representative of an intensity of the x-ray beam 28 as it passes through the patient 26. In one embodiment, the detector array can include a x-ray conversion layer configured to convert x-ray radiation into light. In another embodiment, the detector array can include a photoconductor, which generates electron-hole-pairs or charges in response to x-ray. The detector array may include different kinds of radiation sensors corresponding to different radiation beam sources. In one embodiment, the detector array has a resolution of 1024×768, and therefore, can generate an image frame having 768 lines of pixels with each line having 1024 pixels. In another embodiment, the detector array has a resolution of 2048×1536. Detector arrays having other resolutions can also be used.

In one embodiment, the detector array is capable of detecting images of tissues in the patient 26 formed by the X-ray beams at either or both of the MeV energy level and the keV energy level. In accordance with another embodiment, the detector array includes a single image detecting device that is capable of detecting images formed by beams at multiple energy levels. By way of example, U.S. patent application Ser. No. 10/013,199 entitled "X-RAY IMAGE ACQUISITION APPARATUS" and filed on Nov. 2, 2001 discloses an X-ray image detecting device that is capable of detecting multiple energy level X-ray images and can be used as projection detector in accordance with the present invention. U.S. patent application Ser. No. 10/013,199 is incorporated herein by reference in its entirety.

It should be noted that the radiation system 20 is not limited to having one detector array. In alternative embodiments, the radiation system 20 may include two or more image detectors. For example, multiple image detectors can be used for providing stereotactic image data. In one embodiment, the detector array includes two image detecting devices, one for detecting images formed by the keV image beams, and the other for detecting images formed by the MeV radiation beams. The image detector 40 can also include other types of detector in alternative embodiments.

Although the image detector 40 has been described as a part of the radiation system 20, in alternative embodiments, the image detector 40 can be a part of an imaging device that is separate from the radiation system 20. For example, the image detector 40 can be a digital camera, an infrared camera, or other types of imaging apparatus.

Returning to FIG. 1, the data integration module 55 will now be described in further detail. The data integration module 55 is configured to combine operation data associated with an operation of the radiation system 20 with image data generated by the image detector 40, and storing the combined data in a memory 100. Although the memory 100 is shown as a separate component from the data integration module 55, alternatively, the memory 100 can be a part of the data integration module 55. The data integration module 55 includes a trigger control 60 for controlling a timing of when image data is collected from the image detector 40, an interface 70 for collecting and/or formatting operation data generated by the radiation system 20, an integrator 80 for combining the operation data and the image data, and an image processor 90 for processing the combined machine and image data. It should be noted that any or a combination of the trigger control 60, the interface 70, the integrator 80, and the image processor 90, can be implemented using a hardware (e.g., a processor), a software, or a combination thereof. For example, in one embodiment, the trigger control 60, the interface 70, and the integrator 80 are implemented using a universal control board (UCB), which is a PCI card developed by Varian Medical Systems, Inc., referenced herein, and the image processor 90 can be implemented using a frame processing board (FPB). The UCB can be, for example, a configurable logic device that is implemented using a field programmable gate array (FPGA). Although the trigger control 60, the interface 70, the integrator 80, and the image processor 90 are depicted as separate components in the illustrated embodiment, alternatively, a combination of these components can be implemented as a single component. For example, in one embodiment, the entire data integration module 55 can be implemented using a processor, a computer, or a combination of hardware and software.

The system 10 may further include a work station 30 coupled to the data integration module 55. The work station 30 has a display 32 for presenting data or information, and a user interface 34, such as a keyboard and/or a mouse, which allows a user to control an operation of the data integration module 55 and/or the radiation system 20.

It should be noted that the system 10 in accordance with the present invention is not limited to having the structure as describe herein above. For example, the beam source 22 is not limited to generating X-ray radiation at the keV and/or MeV energy levels. Depending on the nature of treatment or application, the radiation beam source 22 may generate X-ray radiation at other energy spectrums or generate other kinds of radiation beams, which include, but are not limited to, beta ray beams, positron beams, proton beams, antiproton beams, neutron beams, heavy ion beams, e.g., alpha ray beams, carbon ion beams, etc.

Figure 2:
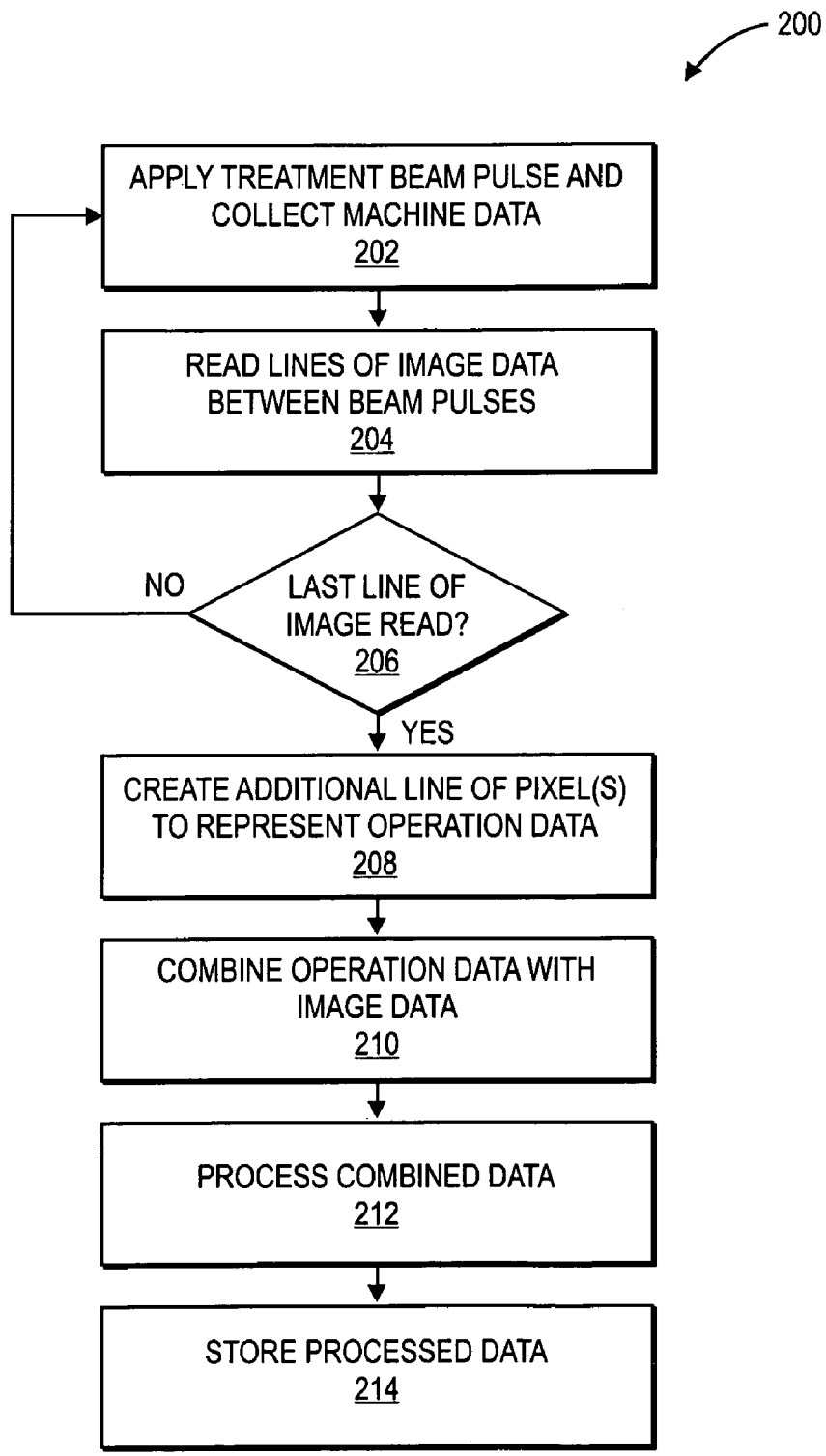
FIG. 2 is a flowchart showing a process for collecting and combining operation data and image data in accordance with an embodiment of the invention.

Methods of using the system 10 will now be described. FIG. 2 shows a process 200 for obtaining and combining image data and operation data during a treatment session. When using the system 10 in a radiation treatment session, the beam source 22 of the radiation system 20 directs a treatment beam 28 (e.g., having an energy level that is in the mega-electron-volt (MeV) range) towards a target region within the patient 26, while the image detector 40 captures images of the target region (step 202). In the illustrated embodiment, the image detector 40 includes a detector array that is secured to the radiation system 20. The treatment beam 28 can be a serious of short pulses. In one embodiment, the treatment beam 28 has a pulse width that is approximately 5 us, and a pulse gap of approximately 2.8 ms. However, the treatment beam 28 can have other durations of pulse width and/or pulse gap.

While the radiation system 20 is being operated, the interface 70 of the data integration module 55 captures operation data from the radiation system 20. As used in this specification, the term "operation data" refers to any data or information associated with an operation, status, or condition of a system (e.g., the system 10), a machine (e.g., the radiation system 20), a subsystem or a component of the system or the machine, or a processor. For examples, the operation data can include one or a combination of a gantry angle, a patient position, a patient orientation, radiation dose rate, radiation dose fraction, beam pulse rate, beam energy, time when beam was activated, time when beam was deactivated, beam variation (if any) during an image readout, machine axis information (e.g., couch position, support arm position, collimator rotation, position of each leaf of a collimator), machine status information (e.g., machine ready, standby, etc.), and other operation data from similar machine, such as the RPM system. In one embodiment, the interface 70 and/or the trigger control 60 may control when and/or how operation data are captured. For example, the interface 70 may capture the gantry angle at a rising edge of a beam pulse (i.e., when the beam pulse is applied). On the other hand, the interface 70 may obtain a total radiation dose rate by integrating radiation dose rate over the entire beam pulse. It should be understood by those skilled in the art that a operation data can be captured before an application of a beam pulse, during an application of a beam pulse, after an application of a beam pulse, or be integrated over a time period, depending on the particular data or information desired to be captured during an operation of the radiation system 20. After the operation data are captured, the interface 70 may process the operation data into a desired format, and stores the operation data in a memory, such as a RAM, for later use. In one embodiment, the operation data are transmitted to the integrator 80.

After a beam pulse has been applied, and before the next beam pulse is activated, lines of image data are collected from the image detector 40 (step 204). In the illustrated embodiment, in order to reduce an artifact that may result in an image, image data is not collected while a beam pulse is being applied. In such case, the trigger control 60 is used to determine when and how image data is to be collected from the image detector 40. In one embodiment, the trigger control 60 is configured to wait for a duration (e.g., between 0.5 and 2.0 ms) after a beam pulse before reading lines of image data from the image detector 40. The wait duration allows photons in the sensors of the detector to decay such that artifacts in an image can be prevented or reduced. Depending on how much time is left between beam pulses, not all lines of image data in an image frame may be collected. For example, assuming a pulse gap of 2.8 ms and a wait duration of 0.8 ms, the system 10 only has 2.0 ms left to read image data between beam pulses. 2.0 ms may not be enough to read an entire frame of image data (e.g., from a whole detector). In such case, the trigger control 60 controls the number of lines of image data that can be read out from the image detector 40 based on the pulse rate and the pulse gap of the treatment beam, and the image readout rate. For example, if 2.0 ms is only enough to read out thirty lines of image data, the trigger control 60 then read out lines 1–30 of image data after a first beam pulse and the first wait period, lines 31–60 of image data after a second beam pulse and the second wait period, and so forth, until the last line of image data is read. As can be seen, when using the system 10 for treatment purposes, the trigger control 60 coordinates how and when image data are read out such that the application of the treatment beam 28 is not affected by the readout process. This ensures that a desired amount of beam energy is delivered to the target region within the patient 26.

It should be noted that the manner in which the operation data and image data are collected should not be limited to the example discussed previously, and that the operation data and image data can be collected using other algorithms, depending on the particular radiation system employed, the type of imaging device used, and/or a particular application. For example, in an alternative embodiment, image data can be collected immediately after a beam pulse without waiting for a duration. Also in another embodiment, image data can be collected while a beam pulse is being applied.

In the illustrated embodiment, image data is transmitted from the image formatter 50 through the integrator 80 to the image processor 90 line by line (step 206). The data integration module 55 determines if the last line of image frame has been transmitted to the image processor 90. If it is determined that the last line of an image frame has been transmitted to the image processor 90, the integrator 80 then creates an additional line (such as a row or a column) of image data, at least a portion of which represents the operation data (step 208). Particularly, at least a portion of the additional line of image data represents the captured operation data that are desired to be combined with the image data of the image frame.

In one embodiment, each pixel of the additional line represents a 16 Bit value. Depending on the information stored, each pixel data may represent different information. In one embodiment, a 16 bit value represents operation data. For example, Bit 0 can represent beam on or beam off information, with 1=Beam on, and 0=Beam off. In another example, Bit 2 can represent beam variation with 1=Beam changed during readout, and 0=Beam did not change during readout. In yet another example, Bit 5 can represent gating signal with 1=Gate closed, and 0=gate open. In another embodiment, operation data is represented by two or more 16 bit values.

Since more than one beam pulse may have been applied for each frame of image, additional pixels may be added to represent data or information associated with different beam pulses that was generated during a particular frame of image. In another embodiment, the operation data can also be represented by a plurality of lines (e.g., rows or columns) of pixels in an image frame. In another embodiment, the operation data can be associated with a particular frame of image using a marker. Other methods of combining data and associating data can also be used to combine or associate the operation data with the image data.

In the image processor 90, the image data and the additional line of pixels are combined and stored as an image frame (step 210). Alternatively, the image data and the additional line of pixels can be combined and stored in the integrator 80, and the combined data is then transmitted to the image processor 90 for processing.

Next, the image processor 90 processes the combined data (step 212). For example, the image processor 90 may correct an offset of a pixel, and/or a gain difference of a pixel. The image processor 90 may also replace an undesirable pixel with a desired pixel, such as, by performing pixel averaging. The image processor 90 may also perform other types of image processing that are known in the art. In one embodiment, the image processor 90 may perform a histogram over an image frame, and provide feedback signal to the radiation system 20 to control an application of the radiation beam. In an alternative embodiment, step 212 may not be required. In such case, the data integration module 55 does not include the image processor 90.

After the combined data has been processed, the combined data is then stored in the memory 100 (step 214). In one embodiment, as the combined data is stored, the operation data is converted into a header associated with the corresponding image frame.

As can be appreciated by those skilled in the art, capturing operation data and image data and combining them in substantially real time (shortly after the data is generated, as governed by machine readout time and processing time) using the data integration module 55 is beneficial in that it reduces the number of systems required to generate the combined data. Combining operation data and image data during the same radiation session is also advantageous in that the combined data can be made available for immediate feedback. The above described system and method also prevent or reduce the risk of lost of data, misfiled data, and incorrect correlation of data, since the collected data are processed automatically by the system 10. Also, compatibility problems associated with combining different data sets from different machines are reduced.

Figure 3:
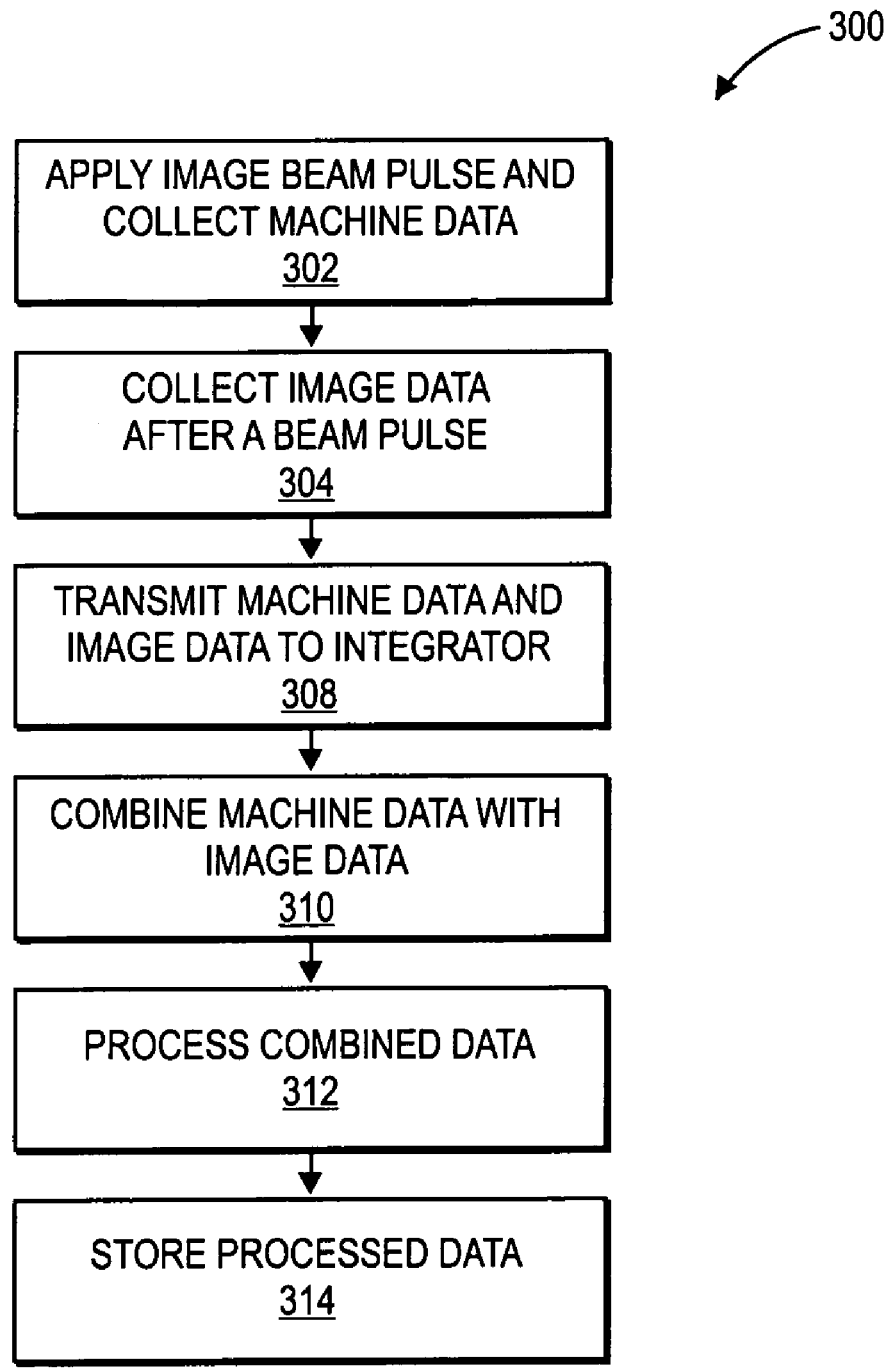
FIG. 3 is a flowchart showing a process for collecting and combining operation data and image data in accordance with another embodiment of the invention.

FIG. 3 shows a process 300 for obtaining and combining image data and operation data during a non-treatment session, such as during a diagnostic, a radiation treatment planning, or a treatment plan verification session. When using the system 10 in a non-treatment session, the trigger control 60 initially triggers the radiation system 20 to activate the beam source 26 for a prescribed duration (step 302). In one embodiment, the image beam comprises a beam pulse having a pulse width that is approximately 10 millisecond. However, the image beam can have other durations of pulse width such that an image with a desired quality can be obtained. When the beam source 26 is activated, the beam source 26 directs an image beam (e.g., having an energy level that is in the kilo-electron-volt (keV) range) towards a target region within the patient 26, while the image detector 40 captures images of the target region. As similarly discussed previously, while the radiation system 20 is being operated, the interface 70 of the data integration module 55 captures operation data from the radiation system 20, and stores the captured operation data in a memory, such as a RAM.

After the beam pulse has been applied for the prescribed duration, the image data of the entire image frame is read out from the image detector 40 (step 304), and the image data together with the captured operation data are then transmitted to the integrator 80 (step 308). Particularly, captured operation data that are desired to be combined with the image data of the image frame are transmitted to the integrator 80. If desired, the image frame can be time stamped before being transmitted to the integrator 80.

Next, the operation data from the radiation system 20 are combined with the image data from the image detector 40 (step 310). As similarly discussed previously, the operation data can be attached as a line of pixels to a frame of image data, represented by a plurality of lines of pixels in an image frame, or associated with a particular frame of image using a marker. Other methods of combining data and associating data can also be used to combine or associate the operation data with the image data.

Next, the combined data is further processed (step 312). As similarly discussed previously, the image processor 90 may correct an offset of a pixel, correct a gain difference of a pixel, replace an undesirable pixel with a desired pixel, and/or perform other types of image processing that are known in the art. In one embodiment, the image processor 90 may perform a histogram over an image frame, and provide feedback signal to the radiation system 20 to control an application of the radiation beam.

After the combined data has been processed, the combined data is then stored in the memory 100 (step 314). In one embodiment, as the combined data is stored, the operation data is converted into a header associated with the corresponding image frame.

It should be noted that the manner in which the operation data and image data are collected should not be limited to the example discussed previously, and that the operation data and image data can be collected using other algorithms, depending on the particular radiation system employed, the type of imaging device used, and/or a particular application. For example, in an alternative embodiment, the operation data and the image data can be collected continuously while an image beam pulse is being applied. In another embodiment, the operation data and the image data can be collected continuously regardless of whether the image beam pulse is being applied. In such case, no synchronization or coordination between the radiation system 20 and the image detector 40 is required, and the system 10 may not include the trigger control 60. Information regarding whether the beam source 22 is activated can be stored as a operation data together with the image data.

COMPUTER SYSTEM ARCHITECTURE

Figure 4:
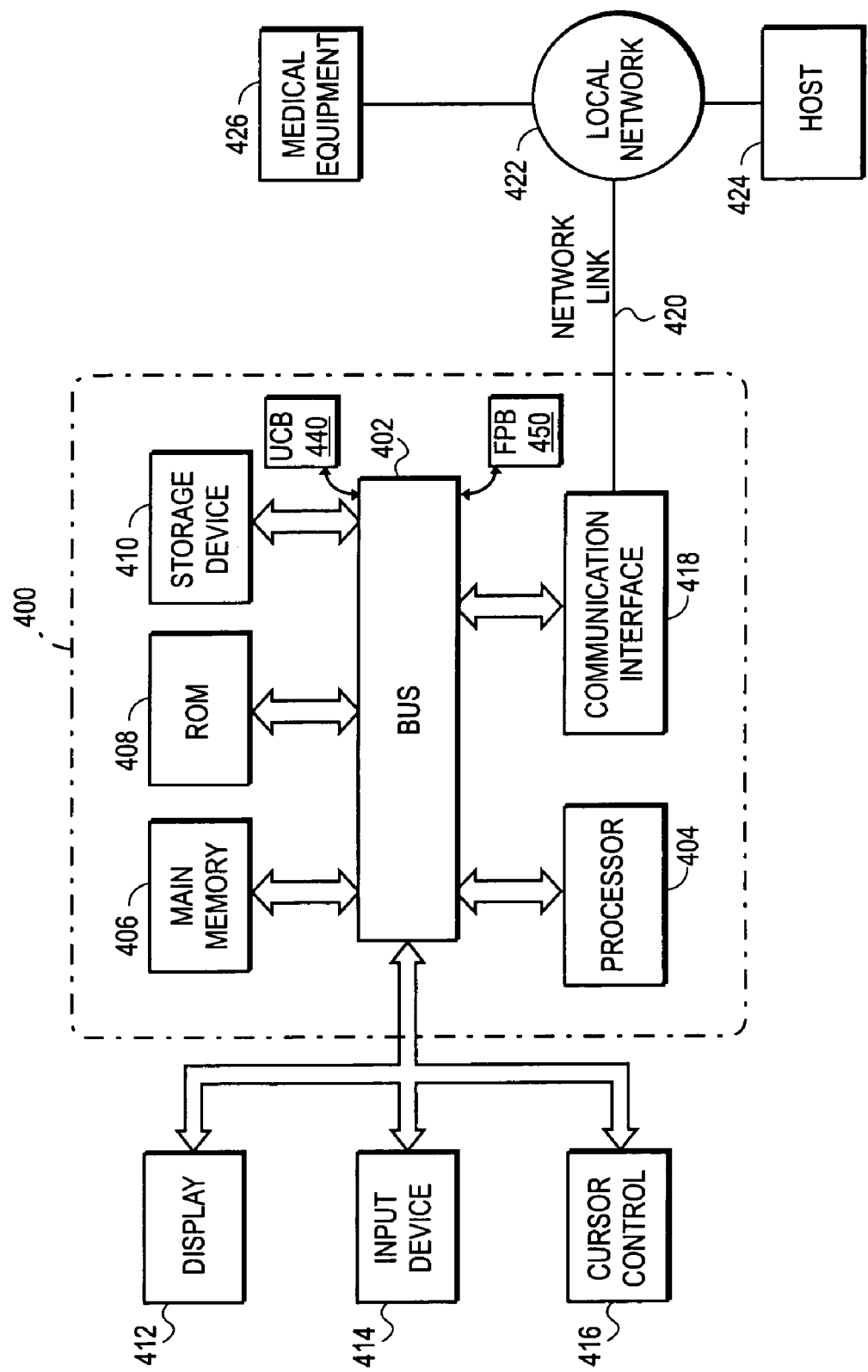
FIG. 4 is a diagram of a computer hardware system with which embodiments of the present invention can be implemented.
Figure 1:
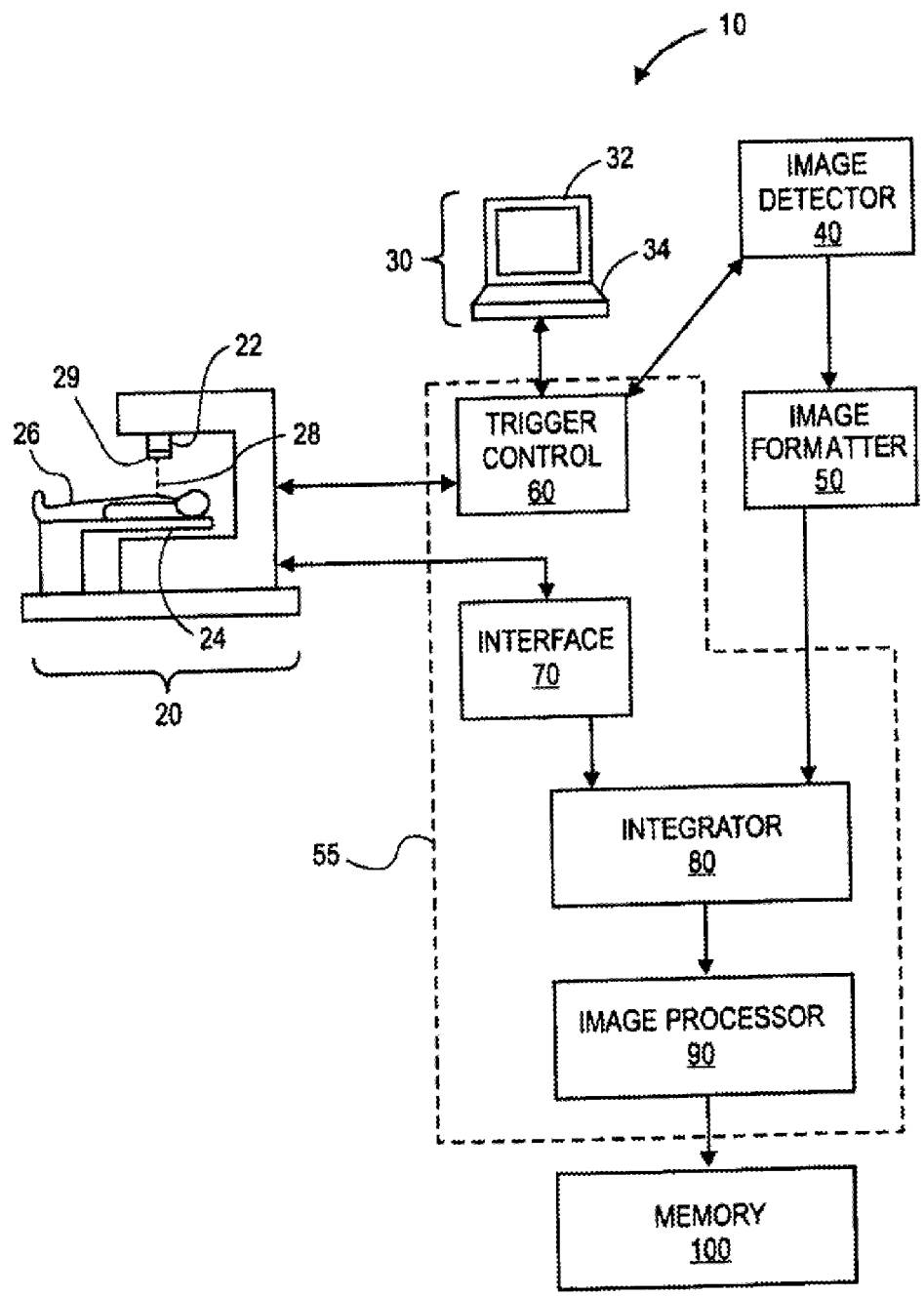
Figure 2:
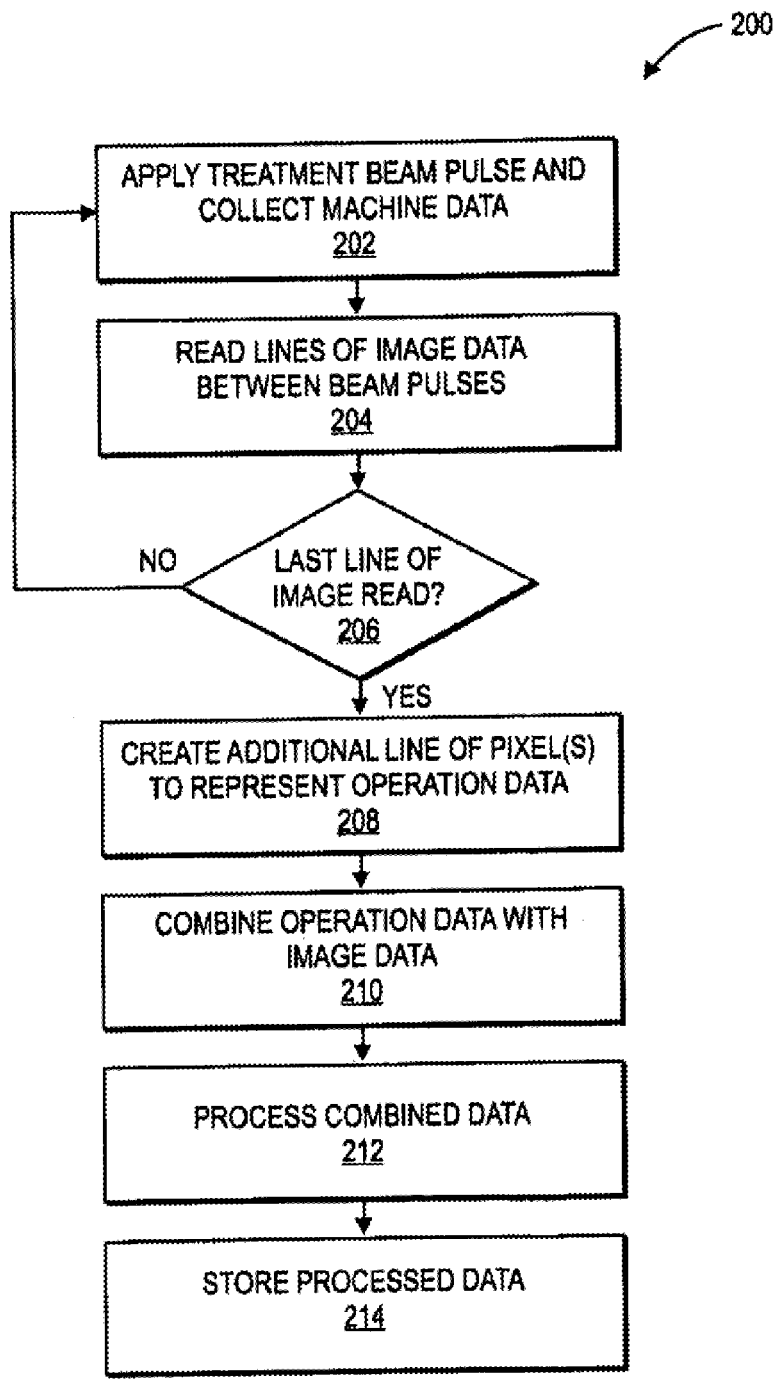
Figure 3:
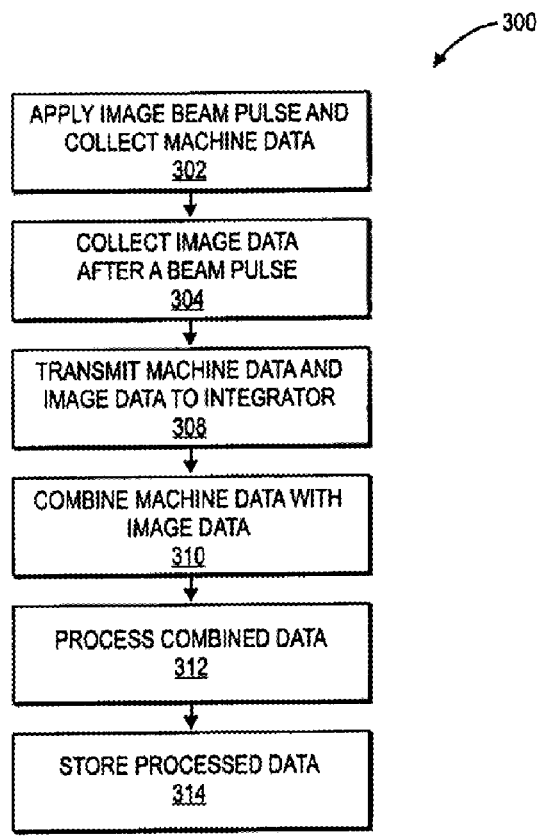
Figure 4:
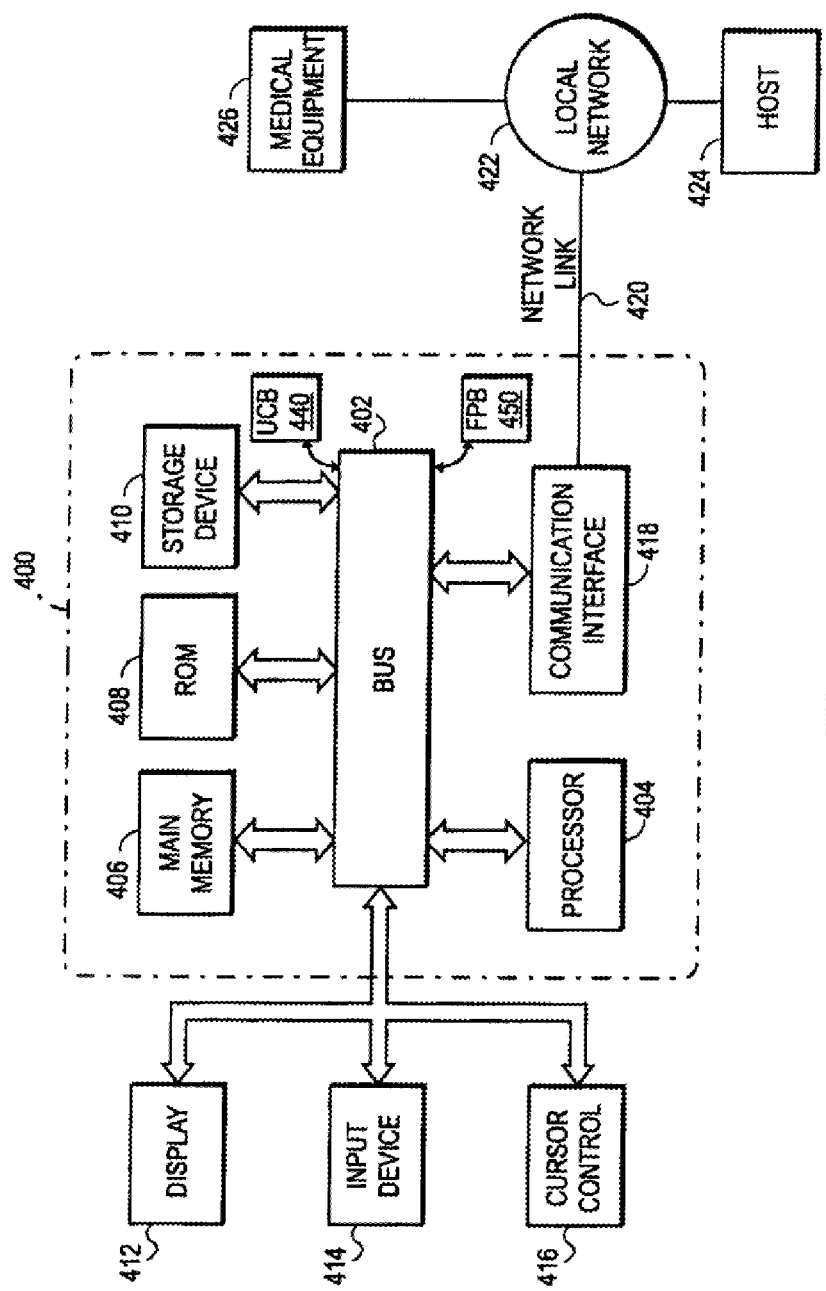

FIG. 4 is a block diagram that illustrates an embodiment of a computer system 400 upon which an embodiment of the invention may be implemented. Computer system 400 includes a bus 402 or other communication mechanism for communicating information, and a processor 404 coupled with the bus 402 for processing information. The computer system 400 also includes a UCB 440 and a FPB 450 coupled to the bus 402. As discussed herein, the UCB 440 is used to implement the trigger control 60, the interface 70, and the integrator 80, and the FPB 450 is used to implement the image processor 90 in one embodiment. The computer system 400 further includes a main memory 406, such as a random access memory (RAM) or other dynamic storage device, coupled to the bus 402 for storing information and instructions to be executed by the processor 404. The main memory 406 also may be used for storing temporary variables or other intermediate information during execution of instructions to be executed by the processor 404. The computer system 400 further includes a read only memory (ROM) 408 or other static storage device coupled to the bus 402 for storing static information and instructions for the processor 404. A data storage device 410, such as a magnetic disk or optical disk, is provided and coupled to the bus 402 for storing information and instructions.

The computer system 400 may be coupled via the bus 402 to a display 412, such as a cathode ray tube (CRT), for displaying information to a user. An input device 414, including alphanumeric and other keys, is coupled to the bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

The computer system 400 can be used to process data. According to one embodiment of the invention, such use is provided by computer system 400 in response to processor 404 executing one or more sequences of one or more instructions contained in the main memory 406. Such instructions may be read into the main memory 406 from another computer-readable medium, such as storage device 410, or from another memory unit. Execution of the sequences of instructions contained in the main memory 406 causes the processor 404 to perform the process steps described herein. One or more processors in a multi-processing arrangement may also be employed to execute the sequences of instructions contained in the main memory 406. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 404 for execution. Such a medium may take many forms, including but not limited to, non-volatile media, volatile media, and transmission media. Non-volatile media includes, for example, optical or magnetic disks, such as the storage device 410. Volatile media includes dynamic memory, such as the main memory 406. Transmission media includes coaxial cables, copper wire and fiber optics, including the wires that comprise the bus 402. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 404 for execution. For example, the instructions may initially be carried on a magnetic disk of a remote computer. The remote computer can load the instructions into its dynamic memory and send the instructions over a telephone line using a modem. A modem local to the computer system 400 can receive the data on the telephone line and use an infrared transmitter to convert the data to an infrared signal. An infrared detector coupled to the bus 402 can receive the data carried in the infrared signal and place the data on the bus 402. The bus 402 carries the data to the main memory 406, from which the processor 404 retrieves and executes the instructions. The instructions received by the main memory 406 may optionally be stored on the storage device 410 either before or after execution by the processor 404.

The computer system 400 also includes a communication interface 418 coupled to the bus 402. The communication interface 418 provides a two-way data communication coupling to a network link 420 that is connected to a local network 422. For example, the communication interface 418 may be an integrated services digital network (ISDN) card or a modem to provide a data communication connection to a corresponding type of telephone line. As another example, the communication interface 418 may be a local area network (LAN) card to provide a data communication connection to a compatible LAN. Wireless links may also be implemented. In any such implementation, the communication interface 418 sends and receives electrical, electromagnetic or optical signals that carry data streams representing various types of information.

The network link 420 typically provides data communication through one or more networks to other devices. For example, the network link 420 may provide a connection through local network 422 to a host computer 424 or to medical equipment 426 such as a radiation beam source or a switch operatively coupled to a radiation beam source. The data streams transported over the network link 420 can comprise electrical, electromagnetic or optical signals. The signals through the various networks and the signals on the network link 420 and through the communication interface 418, which carry data to and from the computer system 400, are exemplary forms of carrier waves transporting the information. The computer system 400 can send messages and receive data, including program code, through the network(s), the network link 420, and the communication interface 418.

Although the system 10 and methods 200 and 300 have been discussed with reference to collecting and combining operation data and image data, the scope of the invention should not be so limited. In alternative embodiments, similar systems and methods may be employed to collect and combine other types of data. For example, in another embodiment, the system may include a camera and a fluoroscope (or a CT system). The camera may be used to sense a marker block placed externally on a patient to thereby monitor a physiological movement of the patient, while the fluoroscope (or the CT system) is used to capture images of an internal tissue of the patient. The image data from the camera can be collected and combined with the image data from the fluoroscope (or the CT system) using the above described method or a similar method. Monitoring patient's movement using a camera and a marker block has been discussed in U.S. patent application Ser. Nos. 09/178,383, and 10/234,658, the entire disclosures of which are expressly incorporated by reference herein.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, any or a combination of the operations performed by the data integration module 55 can be performed by hardware, software, or combination thereof within the scope of the invention, and should not be limited to particular embodiments comprising a particular definition of "processor". The specification and drawings are, accordingly, to be regarded in an illustrative rather than restrictive sense. The present inventions are intended to cover alternatives, modifications, and equivalents, which may be included within the spirit and scope of the present inventions as defined by the claims.

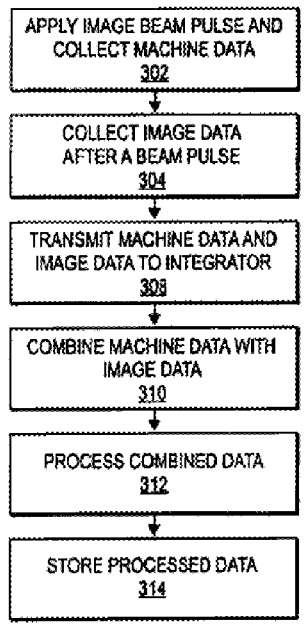

What is claimed is:

1. A method of processing data in a radiation procedure, the method comprising:
    obtaining a first set of image data;
    obtaining operation data;
    putting the operation data into a format that is the same as a format of the first set of image data; and
    adding the operation data to the first set of image data.

2. The method of claim 1, wherein the obtaining the first set of image data comprises reading the first set of image data from a detector array.

3. The method of claim 1, wherein the obtaining the first set of image data comprises collecting the first set of image data from a camera.

4. The method of claim 1, wherein the operation data comprises one or a combination of a gantry angle, a patient position, a patient orientation, radiation dose rate, radiation dose fraction, beam pulse rate, beam energy, time when beam was activated, time when beam was deactivated, beam variation during an image readout, machine axis information, and machine status information.

5. The method of claim 1, wherein the putting comprises formatting the operation data into a second set of image data.

6. The method of claim 5, wherein the formatting comprises converting the operation data into a line of pixels.

7. The method of claim 1, wherein the obtaining the operation data comprises applying a radiation beam pulse using a radiation system, and collecting data associated with an operation of the radiation system.

8. The method of claim 7, wherein the radiation beam pulse has an energy level that is in the kilo-electron-volts range.

9. The method of claim 7, wherein the radiation beam pulse has an energy level that is in the mega-electron-volts range.

10. The method of claim 7, wherein the radiation beam pulse is being used to deliver a radiation treatment dose to a patient.

11. The method of claim 10, wherein the obtaining the first set of image data comprises determining a number of lines of image data that can be read from a detector array within a period.

12. The method of claim 11, wherein the period comprises a time gap between the radiation beam pulse and a next radiation beam pulse.

13. The method of claim 11, wherein the period is determined by subtracting a wait duration from a time gap between the radiation beam pulse and a next radiation beam pulse.

14. The method of claim 11, further comprising reading the number of lines of image data from the detector array.

15. The method of claim 7, wherein the radiation beam pulse is being used to obtain a x-ray image of an object.

16. The method of claim 15, wherein the obtaining the first set of image data comprises reading all lines of image data from a detector array after the radiation beam pulse has been applied.

17. The method of claim 15, wherein the obtaining the first set of image data comprises reading image data while the radiation beam pulse is being applied.

18. The method of claim 15, wherein the obtaining the first set of image data comprises reading image data while the radiation beam pulse is not being applied.

19. The method of claim 1, wherein the adding is performed in substantially real time.

20. A system for processing data in a radiation procedure, the system comprising:
a radiation system;
an image detector for generating a first set of image data;
a processor coupled to the radiation system, the processor being configured to receive operation data associated with an operation of the radiation system and put the operation data into a format that is the same as a format of the first set of image data; and
a memory for storing the operation data with the first set of image data.

21. The system of claim 20, wherein the image detector comprises a detector array that is a part of the radiation system.

22. The system of claim 20, wherein the image detector is a part of an imaging device that is separate from the radiation system.

23. The system of claim 20, wherein the radiation system comprises a computed tomography (CT) system.

24. The system of claim 20, wherein the radiation system comprises a simulator.

25. The system of claim 20, wherein the operation data comprises one or a combination of a gantry angle, a patient position, a patient orientation, radiation dose rate, radiation dose fraction, beam pulse rate, beam energy, time when beam was activated, time when beam was deactivated, beam variation during an image readout, machine axis information, and machine status information.

26. The system of claim 20, wherein the processor is configured to format the operation data into a second set of image data.

27. The system of claim 20, wherein the operation data comprises one or more data associated with one or more respective radiation beam pulses generated by the radiation system.

28. A system for processing data in a radiation procedure, the system comprising:
means for obtaining a first set of image data;
means for obtaining operation data;
means for putting the operation data into a format that is the same as a format of the first set of image data; and
means for adding the operation data to the first set of image data.

29. The system of claim 28, wherein the means for obtaining the operation data comprises a radiation system for applying a radiation beam pulse, and an interface for collecting data associated with an operation of the radiation system.

30. The system of claim 29, wherein the radiation beam pulse is being used to deliver a radiation treatment dose to a patient.

31. The system of claim 29, wherein the means for obtaining the first set of image data comprises a processor for determining a number of lines of image data that can be read from a detector array within a period.

32. The system of claim 29, wherein the radiation beam pulse is being used to obtain a x-ray image of an object.

33. The system of claim 32, wherein the means for obtaining the first set of image data comprises means for reading all lines of image data from a detector array after the radiation beam pulse has been applied.

34. The system of claim 32, wherein the means for obtaining the first set of image data comprises means for reading image data while the radiation beam pulse is being applied.

35. The system of claim 32, wherein the means for obtaining the first set of image data comprises means for reading image data while the radiation beam pulse is not being applied.

36. The system of claim 28, wherein the means for putting comprises means for formatting the operation data into a second set of image data.

37. A computer product configured to cause a process to be performed, the process comprising:
obtaining a first set of image data;
obtaining operation data;
putting the operation data into a format that is the same as a format of the first set of image data; and
adding the operation data to the first set of image data.

38. The computer product of claim 37, wherein the adding is performed in substantially real time.

39. A method for processing data in a radiation procedure, the method comprising:
obtaining operation data, the operation data comprises one or a combination of a gantry angle, a patient position, a patient orientation, radiation dose rate, radiation dose fraction, beam pulse rate, beam energy, time when beam was activated, time when beam was deactivated, beam variation during an image readout, machine axis information, and machine status information; and
formatting the operation data into a set of image data.

40. The method of claim 39, wherein the obtaining the operation data comprises applying a radiation beam pulse using a radiation system, and collecting data associated with an operation of the radiation system.

41. The method of claim 40, wherein the radiation beam pulse is being used to deliver a radiation treatment dose to a patient.

42. The method of claim 40, wherein the radiation beam pulse is being used to obtain a x-ray image of an object.

43. The method of claim 39, wherein the operation data comprises one or more data associated with one or more respective radiation beam pulses generated by the radiation system.

44. The method of claim 39, wherein the formatting comprises processing the operation data such that the operation data can be represented by one or more pixels.

45. The method of claim 39, wherein the formatting comprises converting the operation data into one or more lines of pixels.

46. The method of claim 45, wherein the one or more lines of pixels comprises a column or a row of pixels.

47. The method of claim 39, wherein the formatting is performed in substantially real time.

48. A system for processing data in a radiation procedure, the system comprising:
- means for obtaining operation data, the operation data comprises one or a combination of a gantry angle, a patient position, a patient orientation, radiation dose rate, radiation dose fraction, beam pulse rate, beam energy, time when beam was activated, time when beam was deactivated, beam variation during an image readout, machine axis information, and machine status information; and
- means for formatting the operation data into a set of image data.

49. The system of claim 48, wherein the set of image data comprises one or more data.

50. A computer product configured to cause a process to be performed, the process comprising:
- obtaining operation data, the operation data comprises the operation data can include one or a combination of a gantry angle, a patient position, a patient orientation, radiation dose rate, radiation dose fraction, beam pulse rate, beam energy, time when beam was activated, time when beam was deactivated, beam variation during an image readout, machine axis information, and machine status information; and
- formatting the operation data into a set of image data.

51. The computer product of claim 50, wherein the set of image data comprises one or more data.

52. A method for processing data in a radiation procedure, the method comprising:
- obtaining operation data;
- obtaining an image data; and
- combining the operation data and the image data into a data file in substantially real time.

53. The method of claim 52, wherein the operation data comprises one or a combination of a gantry angle, a patient position, a patient orientation, radiation dose rate, radiation dose fraction, beam pulse rate, beam energy, time when beam was activated, time when beam was deactivated, beam variation during an image readout, machine axis information, and machine status information.

* * * * *

UNITED STATES PATENT AND TRADEMARK OFFICE
CERTIFICATE OF CORRECTION

PATENT NO. : 6,999,555 B2
APPLICATION NO. :10/663009
DATED : February 14, 2006
INVENTOR(S) : Morf It is certified that error appears in the above-identified patent and that said Letters Patent is hereby corrected as shown below:

The title page showing the illustrative figure should be deleted to be replaced with the attached title page.

The drawing sheets, consisting of Figs. 1-4, should be deleted to be replaced with the drawing sheets, consisting of Figs. 1-4, as shown on the attached pages.

Signed and Sealed this

Twenty-seventh Day of May, 2008

JON W. DUDAS
*Director of the United States Patent and Trademark Office*

United States Patent
Morf

(10) Patent No.: US 6,999,555 B2
(45) Date of Patent: Feb. 14, 2006

(54) SYSTEMS AND METHODS FOR PROCESSING DATA

(75) Inventor: Daniel Morf, Buch am Irchel (CH)

(73) Assignee: Varian Medical Systems Imaging Laboratory GmbH, (CH)

(*) Notice: Subject to any disclaimer, the term of this patent is extended or adjusted under 35 U.S.C. 154(b) by 92 days.

(21) Appl. No.: 10/663,089

(22) Filed: Sep. 15, 2003

(65) Prior Publication Data
US 2005/0058237 A1 Mar. 17, 2005

(51) Int. Cl.
G01N 23/02 (2006.01)
G01N 23/083 (2006.01)

(52) U.S. Cl. .................. 378/62; 378/901
(58) Field of Classification Search .......... 378/4, 378/8, 15, 19, 62, 65, 901
See application file for complete search history.

(56) References Cited

U.S. PATENT DOCUMENTS

| 5,077,769 A | * | 12/1991 | Franciose | 378/98.2 |
| 6,490,335 B1 | * | 12/2002 | Wang et al. | 378/15 |
| 6,522,714 B1 | * | 2/2003 | Wang et al. | 378/15 |
| 6,856,666 B2 | * | 2/2005 | Lonn et al. | 378/8 |

* cited by examiner

Primary Examiner—David V Bruce
(74) Attorney, Agent, or Firm—Bingham McCutchen LLP

(57) ABSTRACT

A method for processing data in a radiation procedure includes obtaining operation data, and formatting the operation data into a set of image data, wherein the operation data comprises one or a combination of a gantry angle, a patient position, a patient orientation, radiation dose rate, radiation dose fraction, beam pulse rate, beam energy, time when beam was activated, time when beam was deactivated, and beam variation (if any) during an image readout. Also machine axis information, machine status info and operation data from other systems like for instance the RPM system may be included. A method of processing data in a radiation procedure includes obtaining operation data, obtaining an image data, and combining the operation data with the image data in substantially real time.

53 Claims, 4 Drawing Sheets